US006287605B1

(12) United States Patent
Malamud et al.

(10) Patent No.: US 6,287,605 B1
(45) Date of Patent: Sep. 11, 2001

(54) COMPOSITIONS AND METHODS USEFUL IN TREATMENT AND PREVENTION OF HIV-1 INFECTION

(75) Inventors: Daniel Malamud, Merion; Thandavarayan Nagashunmugam, Havertown; Harvey M. Friedman; William Abrams, both of Merion, all of PA (US); Earl J. Bergey, South Dayton, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/293,758

(22) Filed: Apr. 16, 1999

Related U.S. Application Data

(60) Provisional application No. 60/082,159, filed on Apr. 17, 1998.

(51) Int. Cl.[7] .................................................. A61K 35/37
(52) U.S. Cl. ......................... 424/550; 424/537; 436/518; 435/975
(58) Field of Search ..................................... 435/236, 238, 435/975; 436/518; 424/137, 172.1, 537, 550; 530/322, 388.2, 391.1, 395, 396

(56) References Cited

U.S. PATENT DOCUMENTS

| 4,160,452 | * | 7/1979 | Theeuwes ............................. 128/260 |
| 4,256,108 | * | 3/1981 | Theeuwes ............................. 128/260 |
| 4,265,874 | * | 5/1981 | Bonsen et al. ........................ 424/15 |

OTHER PUBLICATIONS

Archibald and Cole, 1990, AIDS Res. Hum. Retroviruses 6:1425–1432.*
Baba et al., 1996, Science 272:1486–1489.*
Barr et al., 1992, J. Am. Dent. Assoc. 123:37–48.*
Bergey et al., 1994 J. Acquired Immune Defic. Syndr. 7:995–1002.*
Bergey et al., 1993, Critic Rev. Oral Biol. 4:467–474.*
Biesbrock et al., 1991, Infect. Immun. 59:3492–3497.*
Bird et al., 1988, Science 242:423–426.*
Bobek et al., 1996, Genomics 31:277–282.*
Chebbi et al., 1997, AIDS 11:927–928.*
Cohen, 1996, Science 272:1421–1422.*
Coppenhaver et al., 1994, N. Engl. J. Med. 330:1314–1315.*
Crombie et al., 1998, J. Exp. Med. 187:25–35.*
Crout et al., 1998, Curr. Opin. Chem. Biol. 2:98–111.*
Demuth et al., 1988, Inf. Immun. 56:2484–2490.*
Demuth et al., 1990, J. Biol. Chem. 265:7120–7126.*
Denny et al., 1991, J. Dent. Res. 70:1320–1327.
Erickson et al., 1983, European J. Biochem. 133:255–261.
Fischl et al., 1987, JAMA 257:640–644.
Fox and Baum, 1986, N. Engl. J. Med. 31:1387.
Fox et al., 1988, J. Am. Dent. Assoc. 116:635–637.
Friedland et al., 1986, N. Engl. J. Med. 314:344–349.
Fultz, 1986, Lancet 2:1215.
Goto et al., 1991, AIDS Res. Human Retro. 7:343–347.
Groopman et al., 1984, Science 226:447–449.
Ho et al., 1985, N. Engl. J. Med. 313:1606.
Huston et al., 1988, Proc. Natl. Acad. Sci. USA 85:5879–5883.
Ito et al., 1998, Curr. Opin. Chem. Biol. 2(6):701–708.
Jay et al., 1990, Anal. Biochem. 185:324–330.
Kimpton and Emerman, 1992, J. Virol. 66:2232–2239.
Levy et al., 1988, Lancet 2:1248.
Liuzzi et al., 1996, AIDS 10:F51–56.
Malamud et al., 1993, AIDS Res. Hum. Retroviruses 9:633–637.
Malamud et al., 1997, Oral Diseases, 3:S58–S63.
Malamud and Friedman, 1993, Crit. Rev. Oral Biol. Med. 4:461–466.
Matsuo et al., 1997, Carboyhdr. Res. 305:401–413.
McNeely et al., 1995, J. Clin. Invest. 96:456–464.
Melvin et al., 1997, Arch. Pediatr. Adolesc. Med. 151:228–232.
Moore et al., 1991, J. Virol. 65:1133–1140.
Moore et al., 1990, Science 250:1139–1142.
Moore et al., 1993, J. Am. Dent. Assoc. 124:67–74.
Morton et al., 1995, Anal. Biochem. 227:176–185.
Murata et al., 1997, Biosci. Biotech. and Biochem. 61:1059–1066.
Nagashunmugam and Friedman, 1996, DNA Cell Biol. 15:353–361.
Nagashunmugam et al., 1997, AIDS Res. Human Retroviruses 13:371–776.
Nagashunmugam et al., 1998, J Inf. Dis 178:1635–1641.
O'Shea et al., 1990, J. Med. Virol. 4:291–296.
Phillips et al., 1994, AIDS 8:1011–1012.
Qureshi et al., 1995, J. Infect. Dis. 171:190–193.
Ramasubba et al., 1991, Biochem. J. 280:341–352.
Reddy and Levine, 1993, Crit. Rev. Oral Biol. Med. 4:315–323.
Robinovitch and Iverson, 1993, Crit. Rev. Oral Biol. Med. 4:455–459.
Schacker et al., 1996, Ann. Intern Med. 125:257–264.
Slomiany et al., 1992, Intl. J. Biochem, 24:1003–1015.
Tabak, 1990, Crit. Rev. Oral Biol. CRC Press, pp. 229–234.
Tabak, 1995, Annu. Rev. Physiol. 57:547–564.
Takano et al., 1992, Anat. Rec. 230:307–318.
Wahl et al., 1997, Oral Diseases 3:S64–S69.
Wahl, et al., 1997, Am. J. Pathol. 150:1275–1284.
Wu et al., 1996, Proc. Natl. Acad. Sci. 93:15030–15035.
Yeh et al., 1992, J.Acq. Defic. Synd. 5:898–903.
Yeung et al., 1993, J. Infect Dis. 167:803–809.

* cited by examiner

Primary Examiner—Jeffrey Stucker
(74) Attorney, Agent, or Firm—Morgan, Lewis & Bockius, L.L.P.

(57) ABSTRACT

The invention includes compositions comprising substantially purified salivary glycoproteins and carbohydrate ligands thereof which are useful in methods for the treatment and prevention of HIV-1 infection. The invention also includes methods for the treatment and prevention of HIV-1 infection comprising contacting a composition of the invention with a human patient. Additionally, the invention includes antibodies and kits useful in the treatment and prevention of HIV-1 infection.

8 Claims, 5 Drawing Sheets

ALCIAN BLUE/SILVER

SAG →
MG2 →

KDA
175
83
62

SILVER STAIN 1 2 3 4 5 6 7 8 9 10 11
FRACTION NO.

175
83
62
48
33
25

COMPOSITIONS AND METHODS USEFUL IN TREATMENT AND PREVENTION OF HIV-1 INFECTION

CROSS-REFERENCE TO RELATED APPLICATIONS

This application is entitled to priority pursuant to 35 U.S.C. §119(e) to U.S. Provisional Patent Application No. 60/082,159, which was filed on Apr. 17, 1998.

STATEMENT REGARDING FEDERALLY SUPPORTED RESEARCH AND DEVELOPMENT

This invention was supported in part by U.S. Government funds (NIH Grant Nos. DE09569 and RR00040), and the U.S. Government may therefore have certain rights in the invention.

BACKGROUND OF THE INVENTION

The role of human saliva in modulating the acquisition of HIV infection via the oral route or the transmission of HIV via infected oral secretions is important to our understanding of the transmission of AIDS and the development of effective prevention and treatment methods. Although there have been numerous reports detailing the identification and isolation of HIV nucleotide sequences from oral samples such as saliva (Levy et al., 1988, Lancet 2:1248; Barr et al., 1992, J. Am. Dent. Assoc. 123:39–48; Goto et al., 1991, AIDS Res. Human Retro. 7:343–347), buccal scrapings (Qureshi et al., 1995, J. Infect. Dis. 171:190–193) and gingival crevicular fluid (Chebbi et al., 1997, AIDS 11:927–928; O'Shea et al., 1990, J. Med. Virol. 4:291–296), the isolation of infectious HIV virus from the oral cavity of a patient is rare, and when present, viral titers are low (Barr et al., 1992, J. Am. Dent. Assoc. 123:39–48; Malamud and Friedman, 1993, Crit. Rev. Oral Biol. Med. 4:461–466; Melvin et al., 1997, Arch. Pediatr. Adolesc. Med. 151:228–232). Several reports have demonstrated the presence of HIV nucleotide sequences using PCR in up to 80% of oral samples obtained from seropositive individuals (Liuzzi et al., 1996, AIDS 10: F51–56; Chebbi et al., 1997, AIDS 11:927–928; Goto et al., 1991, AIDS res. Human Retro. 7:343–347; Qureshi et al., 1995, J. Infect. Dis. 171:190–193). However, infectious virus could only be isolated from less than 5% of these individuals (Barr et al., 1992, J. Am. Dent. Assoc. 123:39–48).

Thus, the infectivity of HIV in saliva is clearly different from other biologic fluids such as blood and semen. This striking discrepancy between the physical evidence for virus in saliva and the lack of infectious virus suggests that saliva contains HIV inhibitors which are effective at blocking infectivity.

It is now generally accepted that incubation of HIV-1 with human saliva results in a marked decrease (about an 80–95% reduction) in viral infectivity assayed in vitro (Fultz, 1986, Lancet ii:1215) and (Fox et al., 1988, J. Am. Dent. Assoc. 116:735–637). This observation has been reproduced in many laboratories (Malamud and Friedman, 1993, Crit. Rev. Oral Biol. Med. 4:461–466; Robinovitch and Iverson, 1993, Crit. Rev. Oral Biol. Med. 4:455–459; Bergey et al., 1993, Crit. Rev. Oral Biol. Med. 4:467–474; McNeely et al., 1995, J. Clin. Invest. 96:456–464; Yeh et al., 1992, J.Acq. Defic. Synd. 5:898–903; Moore et al., 1993, J. Am. Dent. Assoc. 124:67–74). The experiment involves incubating whole, parotid or submandibular saliva from HIV seronegative individuals with HIV-1, and then adding the HIV/saliva mixture to CD4+ cells, and monitoring virus production after 3–10 days. In many cases, the saliva/HIV mixture is filtered prior to addition to the host cells. These studies have demonstrated anti-HIV activity in whole and ductal saliva from both seronegative and seropositive patients. There is evidence that the anti-viral effect is exerted both at the level of the virus (Malamud et al., 1997, Oral Diseases, 3: S58–S63) and at the level of the host cell (Wahl, et al., 1997, Am. J. Pathol. 150:1275–1284; Wahl et al., 1997, Oral Diseases, 3: S64–S69). It has also been reported that submandibular saliva agglutinates HIV, and that this agglutination might be involved in the inhibitory mechanism (Bergey et al., 76 1994, J. Acq. Imm. Defic. Syn. 7:995–1002), and (Malamud et al., 1993, AIDS Res. Human Retro. 9:633–637).

Proteins present in human saliva which have anti-viral activity have been characterized in previous reports. Much of the work has focused on understanding the role of salivary proteins in host defenses. Salivary agglutinin (SAG) is a high molecular weight (MW=350 kDa) mucin-like glycoprotein produced by both parotid and submandibular salivary glands (Demuth et al., 1988, Inf. Immun. 56:2484–2490). It has been reported that this glycoprotein contains about 40% carbohydrate divided equally between N- and O-linked sugars (Demuth et al., 1990, J. Biol. Chem. 265:7120–7126; Takano et al., 1992, Anat. Rec. 230:307–318; Ericson and Rundergren, 1983, Eur. J. Biochem. 133:255–261). While SAG has been referred to as "mucin-like," it is synthesized in serious acinar cells and serious demilunes of mucin producing acini, but not in mucinous acini where high molecular weight salivary mucin (MG1) and low molecular weight salivary mucin (MG2) are synthesized (Takano et al., 1992, Anat. Rec. 230:307–318).

Human submandibular saliva also contains two proteins termed mucins, MG1 (MW>1000 kDa) and MG2 (MW 130 kDa), which have also been reported to have anti-HIV activity (Bergey et al., 1994, J. Acquired Imm. Defic. Syn. 7:995–1002). Both mucins comprise about 70% carbohydrate, which is predominantly O-linked (Tabak, 1995, Annu. Rev. Physiol. 57:547–564) and has extensive microheterogeneity (Reddy and Levine, 1993, Crit. Rev. Oral Biol. Med. 4:315–323). MG2 is a unique gene product expressed only in the submandibular and sublingual glands, and contains at least one N-linked carbohydrate chain. Both MG1 and MG2 are found in coatings of oral surfaces, and serve as a general protective barrier in humans (Tabak, 1990, Crit. Rev. Oral Biol. CRC Press, pp 229–234). Levels of MG2 in whole saliva vary over a 100-fold range in young adults (18–35 years old), and lower values have been reported in older adults (Denny et al., 1991, J. Dent. Res. 70:1320–1327). MG2 has been reported to bind noncovalently with IgA (Biesbrock et al., 1991, Infect. Immun. 59:3492–3497) and fibronectin (Slomiany et al., 1992, Intl. J. Biochem. 24:1003–1015). Recently, the gene for apomucin MG2, designated MUC7, was cloned and mapped to chromosome 4q 13-q21 (Bobek et al., 1996, Genomics 31:277–282). The glycosylated form of the molecule has not yet been expressed in vitro. Considerable information is available on the structure of the gene, the apoprotein, and the glycosylated mucin.

Human saliva appears to inhibit HIV infection by several different mechanisms. Fultz (1986, Lancet 2:1215) demonstrated that incubation of HIV-1 with human or chimpanzee saliva blocks infection of peripheral blood mononuclear cells (PBMCs). Other reports have demonstrated that incubation of virus with saliva causes virus aggregation, as demonstrated by electron microscopy, and subsequent loss of virus titer upon filtration (Fox et al., 1988, J. Am. Dent. Assoc., 116:635–637; Malamud et al., 1993, AIDS Res. Hum. Retroviruses 9:633–637; Archibald and Cole, 1990, AIDS Res. Hum. Retroviruses 6:1425–1432; Bergey et al., 1993, Critic Rev. Oral Biol. 4:467–474; Bergey et al., 1994, J. Acquired Immune Defic. Syndr. 7:995–1002; Yeh et al., 1992, J. Acquired Immune Defic. Syndr. 5:898–903). It has been suggested that salivary mucin mediates this activity, (Bergey et al., 1994, J. Acquired Immune Defic. Syndr. 7:995–1002) present in both whole saliva and submandibular saliva, with the highest activity being observed in submandibular saliva (Malamud et al., 1993, AIDS Res. Hum. Retroviruses 9:633–637). Saliva obtained from many seronegative patients has been shown to exhibit anti-HIV activity in the absence of a filtration step (Nagashunmugam et al., 1997, AIDS Res Human Retroviruses 13:371–376), and the inhibitory activity was demonstrated to be specific for HIV-1, with little or no inhibitory activity being observed to be directed against adenovirus, herpes simplex virus type I (HSV-1), HIV-2 and SIV (Malamud et al., 1993, AIDS Res. Hum. Retroviruses 9:633–637; Nagashunmugam et al., 1997, AIDS Res Human Retroviruses 13:371–376). Another report has identified a salivary protein termed secretory leukocyte protease inhibitor (SLPI) which reduces the susceptibility of monocytes, macrophages and CD4$^+$ T cells to infection by HIV (McNeely et al., 1995, J. Clin. Invest. 96:456–464). In yet another report, the inhibition of HIV infectivity by saliva was attributed to another protein, thrombospondin I (TSP1) (Crombie et al., 1998, J. Exp. Med. 187:25–35).

While epidemiological studies suggest that the oral transmission of HIV is a rare event (Friedland et al., 1986, N. Engl. J. Med. 314:344–349; Fischl et al., 1987, JAMA 257:640–644), several reports have raised the possibility of such transmission. For example, the productive infection of macaques after application of SIV to the back of the tongue has been reported (Baba et al., 1996, Science 272:1486–1489). In another report, individuals at high risk for HIV infection were studied and oral sex was identified as the sole risk factor in four subjects who seroconverted (Schacker et al., 1996, Ann. Intern Med. 125:257–264).

The fact that the isolation of infectious HIV from oral samples is rare (Fox et al., 1988, J. Am. Dent. Assoc. 116:635–637; Ho et al., 1985, N. Engl. J. Med. 313:1606; Fox and Baum, 1986, N. Engl. J. Med. 31:1387; Coppenhaver et al., 1994, N. Engl. J. Med. 330:1314–1315; Groopman et al., 1984, Science 226:447–449; Yeung et al., 1993, J. Infect Dis. 167:803–809; Barr et al., 1992, J. Am. Dent. Assoc. 123:39–480) despite the presence of HIV nucleotide sequences detectable by RNA or DNA amplification techniques (Goto et al., 1991, AIDS Res. Hum. Retroviruses 7:343–347; Phillips et al., 1994, AIDS 8:1011–1012) in 50–80% of saliva samples obtained from HIV seropositive patients strongly suggests that salivary factors capable of inhibiting HIV infectivity may serve to block HIV infection in vivo.

Despite all of the findings described above, there are currently no compositions or methods available for inhibiting HIV-1 infectivity in vivo by the oral route, or for inhibiting the infectivity in vivo of HIV-1 infected oral secretions. Furthermore, there are no available methods for monitoring the susceptibility of a patient to HIV-1 infection by the oral route. Thus, there is an unmet need for compositions and methods which can be used in effective and safe methods for preventing and treating HIV-1 infection, and for monitoring the susceptibility of individuals to HIV-1 infection. The present invention meets these needs.

BRIEF SUMMARY OF THE INVENTION

The invention includes a method of inhibiting the infectivity of HIV-1. The method comprises contacting an HIV-1 virion with a composition comprising a substantially purified preparation of a human salivary agglutinin, and incubating the HIV-1 virion with the human salivary agglutinin for a period of time sufficient to inhibit the infectivity of HIV-1.

The invention also includes a composition having a surface, having a substantially purified preparation of a human salivary agglutinin associated with the surface.

Also included in the invention is a composition comprising a molecule which comprises a carbohydrate ligand of human salivary agglutinin, wherein the molecule is capable of specific binding with HIV-1 gp120.

In one aspect, the molecule which comprises a carbohydrate ligand of human salivary agglutinin is capable of removing gp120 protein from an HIV-1 virion.

In another aspect, the molecule which comprises a carbohydrate ligand of human salivary agglutinin is capable of inhibiting the infectivity of HIV-1.

The invention also includes a method of inhibiting the infectivity of HIV-1. The method comprises a) contacting an HIV-1 virion with a molecule which comprises a carbohydrate ligand of human salivary agglutinin, and b) incubating the HIV-1 virion with the molecule for a period of time sufficient to inhibit the infectivity of HIV-1.

Also included in the invention is a composition having a surface, having a molecule which comprises a carbohydrate ligand of human salivary agglutinin associated with the surface.

Additionally, the invention includes a method for inhibiting the infectivity of HIV-1. The method comprises a) contacting an HIV-1 virion with a composition comprising a substantially purified preparation of human MG2, and b) incubating the HIV-1 virion with the human MG2 for a period of time sufficient to inhibit the infectivity of HIV-1.

Also included in the invention is a composition having a surface, having a substantially purified preparation of human MG2 associated with the surface.

The invention includes a composition comprising a molecule which comprises a carbohydrate ligand of human MG2, wherein the molecule is capable of specific binding with HIV-1 gp120.

In one aspect, the composition comprising a molecule which comprises a carbohydrate ligand of human MG2 wherein the molecule is capable of removing gp120 protein from an HIV-1 virion.

In another aspect, the composition comprising a molecule which comprises a carbohydrate ligand of human MG2 wherein the molecule is capable of inhibiting the infectivity of HIV-1.

The invention also includes a method of inhibiting the infectivity of HIV-1. The method comprises a) contacting an HIV-1 virion with the composition comprising a molecule which comprises a carbohydrate ligand of human MG2 and b) incubating the HIV-1 virion with the composition for a period of time sufficient to inhibit the infectivity of HIV-1.

Also included in the invention is a composition having a surface, having the composition comprising a molecule which comprises a carbohydrate ligand of human MG2 capable of specific binding with HIV-1 gp120 associated with the surface.

The invention further includes an antibody which specifically binds with a protein selected from the group consisting of human salivary agglutinin and human MG2.

Additionally, the invention includes a kit for detecting a protein which inhibits the infectivity of HIV-1. The kit comprises an antibody which specifically binds with a protein selected from the group consisting of human salivary agglutinin and human MG2 and a detection reagent.

In one aspect, the detection reagent of the kit is selected from the group consisting of an enzyme and a radionuclide.

BRIEF DESCRIPTION OF THE DRAWINGS

The foregoing summary, as well as the following detailed description of the invention, will be better understood when read in conjunction with the appended drawings.

FIG. 1A depicts the results of gradient fractionation of virus lysed with Triton X-100. FIG. 1B depicts the results of gradient fractionation of virus incubated with medium. FIG. 1C depicts the results of virus incubated with submandibular saliva. Virus samples were sedimented using a 10–60% sucrose gradient. Twenty fractions were collected from the gradient and numbered from the top of the gradient. Gradient fractions were assessed for levels of p24 and gp120 by ELISA. Levels of p24, indicated by open circles, are expressed as picograms per 5 microliters, and levels of gp120, indicated by closed circles, are expressed as nanograms per milliliter.

FIG. 2A depicts results of fractions electrophoresed through a 6% SDS-PAGE gel and stained for carbohydrate with Alcian Blue-silver. FIG. 2B depicts results of fractions concentrated 10× and electrophoresed on a 10% SDS-PAGE gel and stained with silver.

DETAILED DESCRIPTION OF THE INVENTION

Definitions

Figure 1A:
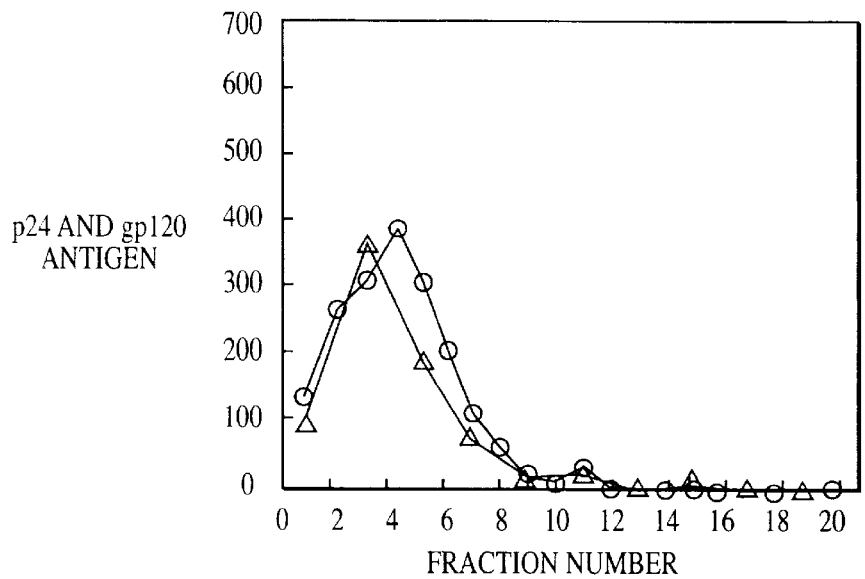
FIGS. 1A–1C are a series of graphs depicting velocity sucrose gradient centrifugation of purified HIV-1 virus.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state. Included within the meaning of the term "substantially pure" as used herein is a compound, such as a protein or polypeptide, which is homogeneously pure, for example, where at least 95% of the total protein (by volume, by wet or dry weight, or by mole percent or mole fraction) in a sample is the protein or polypeptide of interest.

As used herein, the term "specific binding" or "specifically binds" means a protein, such as a glycoprotein, which recognizes and binds the gp120 protein of HIV, but does not substantially recognize or bind other molecules in a sample. The term also means an antibody which recognizes and binds a salivary glycoprotein or a ligand thereof, but does not substantially recognize or bind other molecules in a sample.

As used herein, the term "ligand" means a compound that specifically binds to a target receptor. A "receptor" is a compound that specifically binds to a ligand. A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to an compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

Description

The invention includes the use of a composition comprising substantially purified human salivary agglutinin. Human salivary agglutinin (SAG) is a glycoprotein which is capable of inhibiting the infectivity of HIV-1 as described herein, and thus is useful in methods for the prevention of HIV-1 infection in a patient or for inhibiting the infectivity of HIV-1 containing bodily fluids. SAG is effective in inhibiting HIV-1 infectivity at concentrations present in saliva (i.e. about 0.05 micromolar) as described herein. The carbohydrate composition of acid hydrolyzed SAG as analyzed by Dionex chromatography contained glcNAc, fucose, galactose, sialic acid, mannose, and galNAc at ratios of 1:1:1:1:0.8:0.3, respectively. In addition, the N- and O-linked oligosaccharides released from SAG using Flurophore Assisted Carbohydrate Electrophoresis (FACE, Glyko Inc., Novato, Calif.) were examined. At least 10 structural components were released from SAG which varied in size from 2–18 oligomers, which indicated the complexity of the carbohydrate composition of SAG.

Compositions comprising substantially purified SAG may include SAG alone, or in combination with other salivary proteins or other proteins. SAG may be substantially purified by any of the methods well known to those skilled in the art. Substantially pure protein may be purified by following known procedures for protein purification, wherein an immunological, chromatographic, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The SAG of the invention is, in one embodiment, a component of a pharmaceutical composition which may also comprise buffers, salts, other proteins, and other ingredients acceptable as a pharmaceutical composition.

The invention also includes a carbohydrate ligand of SAG, which is capable of specific binding with a gp120 protein of HIV-1 and inhibiting the infectivity of HIV-1 as described herein. The carbohydrate ligand of SAG may be used as a component of a composition for use in a method for prevention of HIV-1 infection of a patient or in the inhibition of HIV-1 infectivity of biological fluids. For example, the carbohydrate ligand of SAG may be used in lieu of the entire SAG protein in a pharmaceutical composition. Use of the carbohydrate ligand of SAG instead of the full SAG protein results in simplified synthesis and purification procedures in the preparation of a pharmaceutical composition for use as a treatment against HIV-1 infection.

The ligand may be any carbohydrate ligand of human salivary agglutinin capable of specific binding with gp120 protein of HIV-1. For example, the ligand may be an O-linked, or N-linked carbohydrate moiety of the SAG protein. Specific binding of the carbohydrate ligand to the gp120 protein of HIV-1 can be assessed as described in the assays presented in the Experimental Examples section herein. For example, a biosensor assay method may be used. Biosensors record the binding interaction of macromolecules in real time, allowing for the measurement of the affinity constant (KD) as well as the on and off rate constants. One molecule, the ligand, is immobilized and the binding of the second molecule, the analyte, is monitored over time.

The carbohydrate ligand of the invention may be a molecule which comprises the carbohydrate ligand alone, or may include other components, such as protein or other carbohydrate, or another molecule which may be covalently linked to the ligand, or may be non-covalently associated with the ligand.

The carbohydrate ligand of SAG of the invention may be generated by enzymatic digestion or chemical digestion of the full protein SAG. Chemical digestion methods may include, for example, digestion using mild acid hydrolysis or ethylamine hydrolysis. Enzymatic digestion methods may include, for example, digestion using a neuraminidase to release sialic acid, an N-glycanase to release N-linked carbohydrates, or a protease to release glycopeptides. For example, the carbohydrate ligand which specifically binds to gp120 protein of HIV-1 can be assessed using a biosensor assay method and selective removal of carbohydrate residues or protein portions as described herein in the Experimental Examples. The carbohydrate ligand which specifically binds to gp120 can be selectively removed from the human SAG using a specific enzyme, such as a neuraminidase, an N-glycanase, or an O-glycanase to release the carbohydrate ligand which specifically binds to gp120 protein of HIV-1. The role of the removed ligand in specific binding to gp120 protein of HIV-1 can be confirmed using a biosensor assay as described herein in the Experimental Examples.

In another embodiment, the carbohydrate ligand of the invention may be prepared using a biochemical synthesis method. Biochemical methods for synthesizing carbohydrates are well known to those skilled in the art, and may include, for example, using specific glycosyl transferases and selective coupling, using glycosidase-catalyzed transglycosylation, or using a solid-phase oligosaccharide synthesis method (Crout et al., 1998, Curr. Opin. Chem. Biol. 2:98–111; Matsuo et al., 1997, Carbohydr. Res. 305:401–413; Murata et al., 1997, Biosci. Biotech. and Biochem. 61:1059–1066; Ito et al., 1998, Curr. Opin. Chem. Biol. 2(6):701–708).

In another embodiment where the carbohydrate ligand of the invention also includes a protein portion, the carbohydrate ligand and protein portion may be generated, for example, by carrying out a limited proteolysis of the human SAG molecule using a specific protease followed by the use of a glycosidase to result in a carbohydrate ligand of the invention which also comprises a portion of the glycoprotein of human SAG.

In a preferred embodiment, the molecule comprising a carbohydrate ligand of the invention is capable of removing gp120 protein from an HIV-1 virion. The ability to remove gp120 protein from an HIV-1 virion may be assessed using assays described herein in the Experimental Examples section. For example, the virus may be incubated with the molecule comprising a carbohydrate ligand of the invention, placed over a sucrose cushion and centrifuged. The virus pellet obtained is resuspended, concentrated with trichloroacetic acid (TCA) to concentrate the proteins, and aliquots of the pellet and supernatant are analyzed by Western blotting using antibodies to gp120 and p24 (Nagashurmugam and Friedman, 1996, DNA Cell Biol. 15:353–361) or by an ELISA method.

In one embodiment, the molecule comprising the carbohydrate ligand of the invention is capable of inhibiting the infectivity of HIV-1 in a patient by removing gp120 protein from an HIV-1 virion. The molecule comprising the carbohydrate ligand of the invention is included as a component in a pharmaceutical composition which may be administered to a patient to inhibit HIV-1 infectivity or to prevent infection by HIV-1. The inhibition of infectivity of HIV-1 by the molecule comprising the carbohydrate ligand of the invention may be assessed as described herein. Such methods may include p24 assay, reverse transcriptase activity assay or $TCID_{50}$.

The invention also includes the use of a composition comprising substantially purified MG2. MG2 is a glycoprotein which is capable of inhibiting the infectivity of HIV-1 as described herein. Compositions comprising substantially purified MG2 may include MG2 alone, or in combination with other salivary proteins or other proteins. MG2 may be substantially purified by any of the methods well known to those skilled in the art. Substantially pure protein may be purified by following known procedures for protein purification, wherein an immunological, chromatographic, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The MG2 of the invention is, in one embodiment, a component of a pharmaceutical composition which may also comprise buffers, salts, other proteins, and other ingredients acceptable for a pharmaceutical composition.

The invention also includes a carbohydrate ligand of MG2, which is capable of specific binding with a gp120 protein of HIV-1 and inhibiting the infectivity of HIV-1 as described herein. The carbohydrate ligand of MG2 may be used in a composition for use in the inhibition of HIV-1 infectivity, such as a pharmaceutical composition, in lieu of the entire MG2 protein. Use of the carbohydrate ligand of MG2 instead of the entire MG2 protein results in simplified synthesis and purification procedures in the preparation of a pharmaceutical composition for use as a treatment against HIV-1 infection.

The ligand may be any carbohydrate ligand of human MG2 capable of specific binding with gp120 protein of HIV-1. For example, the ligand may be an O-linked, or N-linked carbohydrate moiety of the MG2 protein. Specific binding of the carbohydrate ligand to the gp120 protein of HIV-1 can be assessed as described in the assays presented in the Experimental Examples section herein. For example, a biosensor assay method may be used to assess the strength and kinetics of the binding Biosensors record the binding interaction of macromolecules in real time, allowing for the measurement of the affinity constant ($K_D$) as well as the on and off rate constants. One molecule, the ligand, is immobilized and the binding of the second molecule, the analyte, is monitored over time.

The carbohydrate ligand of the invention may be a molecule which comprises the carbohydrate ligand alone, or may include other components, such as protein or other carbohydrate, or another biocompatible molecule which may be covalently linked to the ligand, or may be non-covalently associated with the ligand.

The carbohydrate ligand of MG2 of the invention may be generated by enzymatic digestion or chemical digestion of the complete MG2 protein. Chemical digestion methods may include, for example, using mild acid hydrolysis or ethylamine. Enzymatic digestion methods may include, for example, digestion using a specific exoglycosidase (e.g., neuraminidase, mannosidase, fucosidase) or a specific endoglycosidase (e.g., N-glycanase, O-glycanase). For example, the carbohydrate ligand which specifically binds to gp120 protein of HIV-1 can be assessed using a biosensor assay method and selective removal of carbohydrate residues or protein portions as described herein in the Experimental Examples. The carbohydrate ligand which specifically binds to gp120 can be selectively removed from the human MG2 using a specific enzyme such as a neuraminidase, an N-glycanase, an O-glycanase or a specific exoglycosidase to release the carbohydrate ligand which specifically binds to gp120 protein of HIV-1. The role of the removed ligand in specific binding to gp120 protein of HIV-1 can be confirmed using a biosensor assay as described herein in the Experimental Examples.

In another embodiment, the carbohydrate ligand of MG2 of the invention may be prepared using a biochemical synthesis method. Biochemical methods for synthesizing carbohydrates are well known to those skilled in the art, and may include, for example, using specific glycosyl transferases and selective coupling, using glycosidase-catalyzed transglycosylation, or using a solid-phase oligosaccharide synthesis method (Crout et al., 1998, Curr. Opin. Chem. Biol. 2:98–111; Matsuo et al., 1997, Carbohydr. Res. 305:401–413; Murata et al., 1997, Biosci. Biotech. and Biochem. 61:1059–1066; Ito et al., 1998, Curr. Opin. Chem. Biol. 2(6):701–708).

In another embodiment where the carbohydrate ligand of the invention also includes a protein portion, the carbohydrate ligand and protein portion may be generated, for example, by carrying out a limited proteolysis of the human MG2 molecule using a specific protease followed by the use of a glycosidase to result in a carbohydrate ligand of the invention which also comprises a portion of the protein of human MG2.

In a preferred embodiment, the molecule comprising a carbohydrate ligand of the invention is capable of removing gp120 protein from an HIV-1 virion. The ability to remove gp120 protein from an HIV-1 virion may be assessed using assays described herein in the Experimental Examples section. For example, the virus may be incubated with the molecule comprising a carbohydrate ligand of the invention, placed over a sucrose cushion and centrifuged. The virus pellet obtained is resuspended, concentrated with trichloroacetic acid (TCA) to obtain concentrated proteins, and aliquots of the pellet and supernatant are analyzed by Western blotting using antibodies to gp120 and p24 (Nagashunmugam and Friedman, 1996, DNA Cell Biol. 15:353–361) or by ELISA (NEN-Dupont).

In one embodiment, the molecule comprising the carbohydrate ligand of MG2 of the invention is capable of inhibiting the infectivity of HIV-1 in a patient by removing gp120 protein from an HIV-1 virion. The molecule comprising the carbohydrate ligand of MG2 of the invention is included as a component in a pharmaceutical composition which may be administered to a patient to inhibit HIV-1 infectivity or to prevent infection by HIV-1. The inhibition of infectivity of HIV-1 by the molecule comprising the carbohydrate ligand of the invention may be assessed as described herein. Such methods may include p24 assay, reverse transcriptase activity assay or $TCID_{50}$.

The invention also includes an antibody which is capable of specifically binding to either human SAG or human MG2. The antibody of the invention may be a monoclonal or a polyclonal antibody, or may be a synthetic, humanized or phage displayed antibody. The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988, Antibodies: A Laboratory Manual, Cold Spring Harbor, N.Y.; Houston et al., 1988, Proc. Natl. Acad. Sci. USA 85:5879–5883; Bird et al., 1988, Science 242:423–426). By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The invention also includes a kit for detecting a protein which inhibits the infectivity of HIV-1. The proteins include human SAG and human MG2. The kit of the invention, may, for example, be an ELISA kit which includes an antibody, a detection reagent, and a reaction surface. In one embodiment, the antibody is an antibody of the invention which specifically binds with either human SAG or human MG2. The antibody may be any type of antibody described herein and may be made using any of the methods described herein. The reaction surface may be a microtiter plate, such as an ELISA plate. The detection reagent may be any detection reagent known to those skilled in the art. For example, the detection reagent may be an enzyme, or a radionuclide. In one embodiment, the kit of the invention is an ELISA kit for detecting the presence of human SAG or human MG2 in a bodily fluid such as saliva of a human patient.

The kit may include a microwell plate, an antibody which is capable of specifically binding either human SAG or human MG2, and a secondary enzyme capable of binding the antibody of the invention and also horseradish peroxidase. The ELISA kit of the invention may be used, for example, to carry out an ELISA assay of a bodily fluid of a patient, such as a saliva sample. The assay may be used to detect and quantify levels of human SAG and human MG2 present in the saliva of the patient. The quantity of human SAG or human MG2 in the patient's saliva may be correlated with the ability of the patient's saliva to inhibit the infectivity of HIV-1.

In another embodiment, the kit of the invention is a Western Blotting or dot blotting kit for detecting the presence of human SAG or human MG2 in a bodily fluid such as saliva of a human patient.

The kits of the present invention may be used, for example, to assess the susceptibility of a patient to HIV-1 infection. Patients with high susceptibility to HIV-1 infection due to low levels of SAG or MG2 may be treated with one of the pharmaceutical compositions of the invention to enhance resistance of these individuals to HIV-1 infection. The correlation between the levels of human SAG or MG2 with the ability of a patient to inhibit the infectivity of HIV-1 is established using the procedures described in the Experimental Examples presented herein.

The invention also includes a method of inhibiting the infectivity of HIV-1 in bodily fluids, or in infective oral secretions. The method is useful in preventing HIV-1 infection, or inhibiting the infectivity of HIV-1. This method can be used, for example to inhibit the infectivity of oral secretions, for example in a hospital setting where medical personnel are exposed to infectious HIV-1 secretions.

In one embodiment, the method comprises contacting an HIV-1 virion with the human SAG compositions described herein. In one embodiment, the human SAG composition may comprise substantially purified human SAG. The sample from a patient containing the HIV-1 virion may be obtained from any sample of bodily fluid, such as a saliva sample, a blood sample, or a semen sample. In one embodiment, a composition comprising substantially purified human SAG is contacted with an HIV-1 virion from a sample of a patient for a period of time sufficient for the human SAG to inhibit the infectivity of HIV-1. The inhibition of the infectivity of HIV-1 can be assessed as described herein in the Examples.

In another embodiment, the method of inhibiting the infectivity of HIV-1 comprises contacting an HIV-1 virion obtained from a bodily fluid sample of a patient with a composition having a surface which contains a substantially purified human SAG associated with said surface. Examples of such surfaces include plastic or other polymer surfaces, which are inert to reaction with bodily fluids, and are considered biocompatible. In one embodiment of the method of the invention, the composition having substantially purified human SAG associated with the surface is contacted with a body fluid of a patient or an infective oral secretion which contains an HIV-1 virion. The composition is contacted or incubated with the sample of bodily fluid containing the HIV-1 virion for a period of time sufficient to inhibit the infectivity of HIV-1. The inhibition of the infectivity of HIV-1 can be assessed by assays as described herein in the Experimental Examples section.

Additionally, the invention includes a method comprising contacting a sample from a patient containing an HIV-1 virion with the human MG2 compositions described herein. In one embodiment, the human MG2 composition may comprise substantially purified human MG2. The sample from a patient containing the HIV-1 virion may be obtained from any sample of bodily fluid, such as a saliva sample, a blood sample or a semen sample. The composition of the invention comprising substantially purified human MG2 is incubated with the sample of a patient containing an HIV-1 virion for a period of time sufficient for the human MG2 to inhibit the infectivity of HIV-1. The inhibition of the infectivity of HIV-1 can be assessed as described herein in the Experimental Examples section. For example, parameters which are used to assess HIV replication, such as, for example, the presence or absence of HIV specific components, such as nucleic acid or protein, or in the latter case, the activity of HIV specific components, such as reverse transcriptase, may be used to assess inhibition of HIV in a sample.

In another embodiment, the method comprises administering to a patient a pharmaceutical composition comprising a substantially purified human MG2 or carbohydrate ligand of human MG2 as either a preventive measure against HIV-1 infection, or to inhibit the infectivity of HIV-1 within a patient infected with HIV-1.

In yet another embodiment, the method of inhibiting the infectivity of HIV-1 comprises contacting an HIV-1 virion obtained from a bodily fluid sample of a patient with a composition having a surface which contains a substantially purified human MG2 associated with said surface. Examples of such surfaces include plastic or other polymer surfaces, which are inert to reaction with bodily fluids, and are considered biocompatible. In one embodiment of the method of the invention, the composition having substantially purified human MG2 associated with the surface is contacted with a body fluid of a patient or an infective oral secretion which contains an HIV-1 virion. The composition is contacted or incubated with the sample of bodily fluid containing the HIV-1 virion for a period of time sufficient to inhibit the infectivity of HIV-1. The inhibition of the infectivity of HIV-1 can be assessed by assays as described herein in the Experimental Examples section.

The invention also includes using a molecule comprising a carbohydrate ligand of the SAG or MG2 of the invention in lieu of the complete SAG or MG2 protein in any of the methods of the invention described above for inhibiting the infectivity of HIV-1.

The invention encompasses the preparation and use of pharmaceutical compositions comprising a compound useful for the prevention of HIV infection or inhibition of HIV infectivity as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Particularly contemplated additional agents include antiemetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, a gel or cream or solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Additional delivery methods for administration of compounds include a drug delivery device, such as that described in U.S. Pat. No. 5,928,195, filed on Jul. 28, 1998.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1
Human Submandiubular Saliva Inhibits HIV-1 Infection by Displacing Envelope Glycoprotein gp120 from the Virus To define the mechanism of inhibition of HIV-1 infection by human submandibular saliva, virus was incubated with saliva or media or substantially purified salivary glycoproteins fractionated by velocity sucrose gradient centrifugation, and analyzed for quantity of the viral proteins p24 and gp120. Submandibular saliva was fractionated by anion exchange chromatography to identify the salivary proteins responsible for the inhibition of HIV-1 infection. After incubation with saliva, the envelope glycoprotein gp120 was displaced from both a laboratory-adapted and a low passage clinical HIV-1 isolate. Protein fractions comprising anti-HIV activity were assayed for their ability to strip gp120 from virus. The substantially purified active fractions were found to contain two high molecular weight sialyated glycoproteins identified as SAG and mucin (MG2), and several lower molecular weight proteins. It thus appears that these specific salivary proteins interact with HIV-1 to strip gp120 from the virus and decrease viral infection in vitro.

The materials and methods used in this Example are now described.

Cells, Viruses and Saliva

Virus stocks were prepared by infecting peripheral blood mononuclear cells (PBMCs) obtained from healthy seronegative donors and isolated by Ficoll Hypaque gradient centrifugation. Cells were stimulated with phytohemagglutinin (2 micrograms per milliliter) for 48 hours and then grown in RPMI medium containing 10% fetal calf serum, interleukin-2 (IL-2) at 10 units/ml and gentamycin at 10 micrograms per milliliter. After 48–72 hours of incubation with IL-2, the cells were infected with HIV. Virus strains used for infection included the laboratory-adapted strain HIV-1$_{HxB2}$ and a low passage HIV-1 isolate (92US076, a syncytial, postpartum infant isolate). The strains were obtained from AIDS Research Reagent and Reference Program. Human submandibular saliva was obtained from HIV seronegative donors and was pooled, dialyzed and lyophilized as described (Malamud et al., 1993, AIDS Res. Hum. Retroviruses 9:633–637; Nagashunmugam et al., 1997, AIDS Res. Human Retroviruses 13:371–376).

Purification of Virus

Supernatant fluid obtained from infected PBMCs was centrifuged at 3000×g, passed through a 0.45 micron filter to remove cellular debris, and centrifuged at 112,700×g for 2 hours at 4° C. through a 5% sucrose cushion. The resulting virus pellet was resuspended in 1 ml of RPMI medium and was fractionated on a Sephacryl 1000 (Pharmacia, Piscataway, N.J.) column to remove free gp120 (Moore et al., 1990, Science 250:1139–1142). The column was eluted with phosphate-buffered saline and fractions obtained from the column were assessed for levels of HIV-1 by infection of PBMCs. The fractions with the highest virus titers were pooled and stored at −70° C.

Antibodies

Monoclonal antibodies to p24 and gp120 were obtained from the AIDS Research Reagent Reference program. Polyclonal antibodies to human SAG (SAG) were prepared as previously described (Takano et al., 1991, Anat. Rec. 230:307–318) and polyclonal antibodies to mucin (MG2) were obtained from Dr. Michael Levine (State University New York, Buffalo).

Analysis of Virus-associated Envelope Glycoproteins

Purified infectious virus (250 nanograms of p24 equivalent) was incubated in a final volume of 500 microliters either with medium or with substantially purified salivary protein fractions, or was lysed using a solution of 0.1% Triton X-100 in PBS. After incubation, the virus samples were placed on a 4.5 ml 10–60% sucrose gradient and centrifuged at 145,000×g for 2.5 hours at 4° C. Fractions (250 microliters) were collected starting from the top of the gradient and analyzed for p24 and gp120 content by ELISA (NEN Dupont, Boston, Mass.).

As an alternative method to measure the removal of gp120 from the virion, virus was incubated with either medium, saliva, or substantially purified salivary protein fractions, placed over a 5% sucrose cushion and centrifuged at 145,000 g for 2.5 hours at 4° C. The virus pellet obtained was suspended in 100 microliters of PBS, and the gradient supernatant was precipitated with 10% trichloroacetic acid (TCA) to concentrate the proteins. Aliquots of the pellet and supernatant were analyzed by Western blotting using antibodies to gp120 and p24 (Nagashurnugam and Friedman, 1996, DNA Cell Biol. 15:353–361) or by ELISA (NEN-Dupont).

Purification of Salivary Proteins by Anion Exchange Chromatography

Lyophilized HIV-1 seronegative saliva was resuspended in 25 mM Tris buffer at pH 8.0 and filtered through a 0.22 micron membrane, applied to a MonoQ HPLC column (Pharmacia, Picscataway, N.J.) and eluted using a 0 to 0.5 molar NaCl linear gradient at 0.5 ml/min. Protein fractionation was monitored by absorbance at 280 nm. Eleven fractions of equal protein concentration were collected, concentrated, and loaded onto 10% or 6% SDS-polyacrylamide gels. The gels were stained with silver (Bio-Rad Laboratories, Richmond, Calif.) or Alcian Blue (Jay et al., 1990, Anal. Biochem. 185:324–330) to visualize proteins or carbohydrates, respectively. Replicate gels were Western blotted and probed with a polyclonal antibody to either MG2 or SAG.

Virus Infectivity Assay

HeLa-CD4LTR-β gal cells were used as target cells to monitor virus infection (Kimpton and Emerman, 1992, J. Virol. 66:2232–2239). Aliquots (200 microliters) of submandibular saliva or anion exchange column fractions were incubated with an equal volume of HIV-1$_{HxB2}$ containing 50 nanograms of virus and administered to target cells for a period of 3 hours. The cells were then washed with PBS and grown in fresh medium. After 48 hours, the cells were fixed and stained with X-gal. The resulting number of blue cells was counted and expressed as percent inhibition by comparing to samples treated with virus alone.

The results of the experiments presented in this Example are now described.

The Effect of Saliva on Viral gp120

Figure 1B:
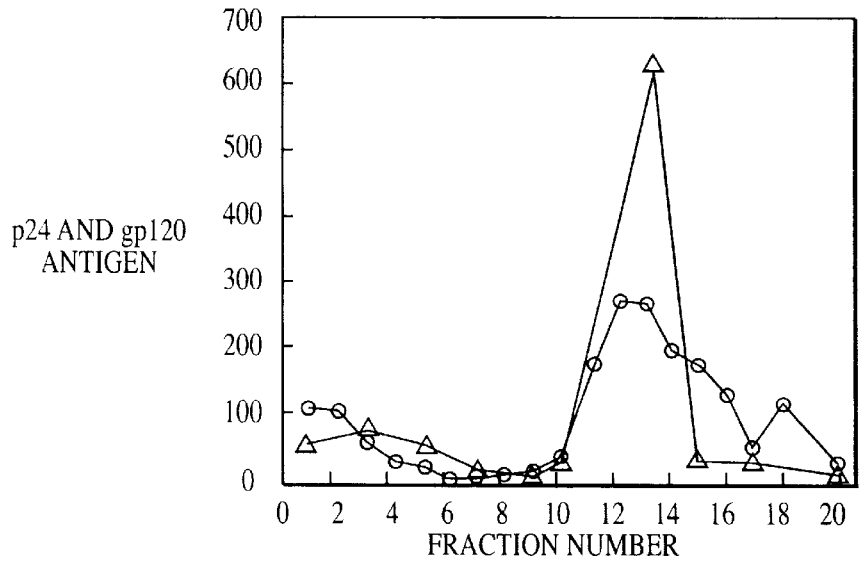
Figure 1C:
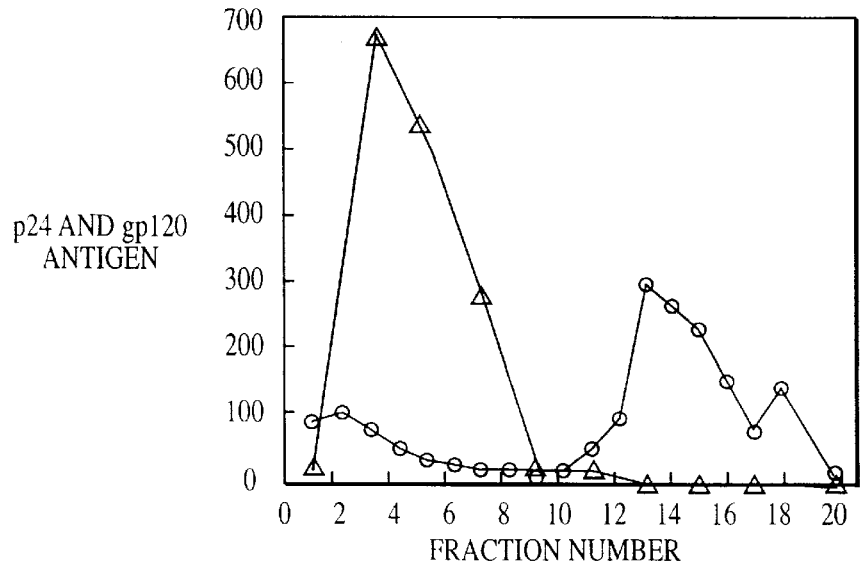
Figure 2A:
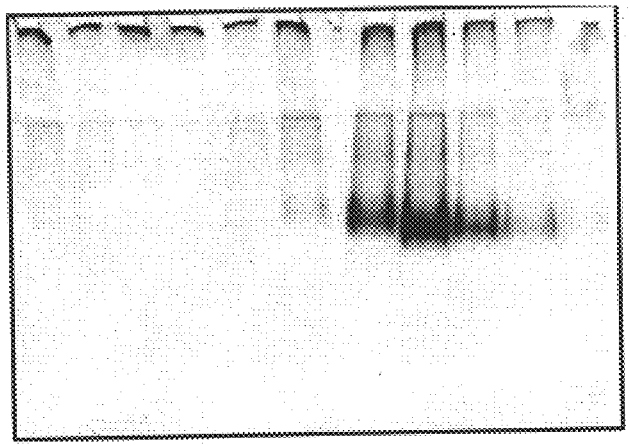
FIGS. 2A and 2B are a pair of images of gels depicting the anion exchange fractionation of human submandibular saliva.
Figure 2B:

Purified HIV-1$_{HxB2}$ was incubated as described herein with submandibular saliva, or, as controls, with medium or Triton X-100. After incubation, the viral samples were placed on a sucrose gradient. When virus was lysed with Triton X-100, the viral proteins p24 and gp120 appeared at the top of the gradient as depicted in FIG. 1A. When virus was incubated with media, gp120 and p24 co-migrated in the gradient as depicted in FIG. 1B. In contrast, when virus was incubated with saliva, gp120 dissociated from the p24 fractions and migrated towards the top of the gradient (the lower fraction numbers) as depicted in FIG. 1C. These results suggest that saliva removes gp120 from the virus.

To confirm this observation and to simplify the assay procedure, purified HIV-1 was incubated with saliva or media, and then centrifuged through a 5% sucrose cushion. After centrifugation, the supernatant and pellet were separated and assayed by Western blotting for p24 and gp120. Supernatants were concentrated by TCA precipitation prior to electrophoresis. In virus samples incubated with medium, both gp120 and p24 remained associated with the virus and appeared in the pellet. In contrast, when virus was incubated with saliva, gp120 was displaced from the virus and appeared in the supernatant.

Anion Exchange Chromatography of Submandibular Saliva

To identify the proteins involved in the inhibition of infectivity of HIV, submandibular saliva was fractionated by anion exchange chromatography on a MonoQ column (Pharmacia, Piscataway, N.J.). The column was eluted with a linear gradient from 0 to 0.5 molar NaCl. Fractions containing equivalent amounts of protein were collected and evaluated for inhibition of HIV infectivity using HeLa-CD4 cells that measure HIV-driven β-galactosidase expression. The anti-HIV activity was observed in fractions 7–9, which inhibited HIV infectivity by about 65–75%. In a separate series of experiments, anion exchange fractions were collected, electrophoresed using SDS-PAGE, and stained with Alcian Blue-silver. The staining revealed two prominent bands that were most intense in fractions 7–9. The bands included a darker staining band with a MW of approximately 130 KDa and a fainter staining band with a MW of approximately 350 KDa, as depicted in FIG. 3A. Western blotting identified the higher molecular weight protein as salivary agglutinin (SAG) and the 130 KDa protein as low molecular weight mucin (MG2). Silver-staining also revealed several lower molecular weight proteins which are shown in FIG. 3B.

The Effect of Substantially Purified Salivary Proteins on a Primary HIV-1 Isolate Laboratory adapted HIV-1 isolates typically dissociate gp120 more readily than low passage clinical isolates (Moore et al., 1991, J. Virol. 65:1133–1140). To determine the effects of submandibular saliva and substantially purified salivary proteins on a low passage clinical isolate (HIV-1, 92US076), the clinical HIV-1 isolate was passaged once in PBMCs to obtain higher virus titer and then purified to remove dissociated gp120. Anion exchange (MonoQ) HPLC column fractions 7–9, which contained substantially purified salivary proteins, were pooled as "Fraction D" and compared with submandibular saliva and medium as a control for gp120 stripping activity. After incubation with either treatment, the mixture of virus with either Fraction D, saliva or medium was centrifuged through a 5% sucrose cushion. Western blotting analysis of the virus pellets for the presence of either or both of p24 and gp120 indicated that treatments using either saliva or substantially purified salivary proteins displaced gp120 from the virus. The amount of gp120 and p24 in the autoradiogram obtained from Western blotting was quantified by densitometry, and the ratio of gp120 to p24 was calculated to provide an estimate of the amount of gp120 removed from the virion. The gp120:p24 ratio of media control was set at a value of 1.0 representing all gp120 being associated with the virion. Incubation of virus samples with saliva removed 79% of the virus associated gp120, while incubation of virus samples with Fraction D removed 68% of the virus associated gp120.

Figure 3:
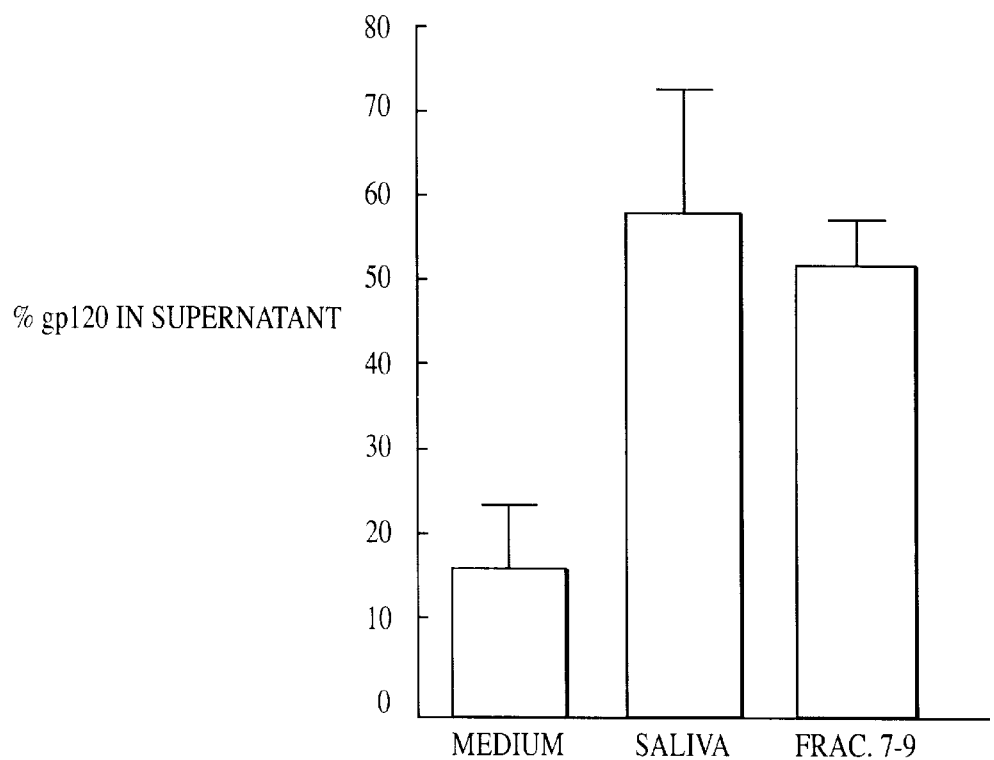
FIG. 3 is a bar graph depicting the levels of dissociated gp120 as assessed by ELISA. Medium, submandibular saliva or substantially purified salivary proteins (Fraction D) were incubated with a purified low passage clinical isolate, centrifuged through a 5% sucrose cushion, and gp120 was quantified by ELISA. Results are expressed as (amount of gp120 detected in the supernatant/total gp120 detected in pellet plus supernatant)×100%. The results are the mean±standard error of three independent experiments.

Since the amount of purified primary clinical isolate loaded in the virus samples was less than that loaded in the case of the laboratory adapted isolate HIV-1$_{HxB2}$, the supernatant collected after the centrifugation of clinical isolate samples contained insufficient gp120 to be detectable by Western blotting. Therefore, gp120 was quantified in supernatant fluids from these samples using an ELISA. Results of the ELISA analysis are shown in FIG. 3. When virus was incubated with media as control, 16% of the total gp120 appeared in the supernatant, as compared with 58% and 52% for saliva and substantially purified saliva, respectively.

Thus, both saliva and substantially purified salivary proteins displaced gp120 from both a laboratory-adapted HIV-1 strain and a low passage clinical HIV-1 isolate.

The results of testing the effect of submandibular saliva and substantially purified submandibular saliva on purified virus particles of both a laboratory adapted and a primary HIV-1 isolate established that gp120 was dissociated from the HIV-1 virion. This indicated that the anti-HIV-1 activity of submandibular saliva acted directly upon the virus. This is consistent with previous reports that preincubation of target cells with saliva does not block HIV-1 infection (Malamud et al., 1997, Oral Diseases 3: (suppl.1)S58–S63). The inhibitory factor(s) described herein thus differ from those of McNeeley et al. (McNeely et al., 1995, J. Clin. Invest. 96:456–464), who reported that anti-HIV activity in human saliva is associated with Secretory Leukocyte Protease Inhibitor (SLPI), which reduces virus infectivity by interacting with surface proteins on host cells (Wahl et al., 1997, Oral Diseases 3: S64–S69).

It has previously been reported that purified salivary MG2 inhibits HIV infection of HeLa-CD4 cells, and that this inhibition is associated with viral aggregation (Bergey et al., 1994 J. Acquired Immune Defic. Syndr. 7:995–1002). Submandibular saliva substantially purified by anion exchange HPLC was shown herein to contain two high molecular weight glycoproteins, MG2 and SAG. These salivary glycoproteins may inhibit infection by both agglutinating virus and dissociating the envelope glycoprotein gp120. Purified MG2 has been reported to interact with gp120, which supports a possible role for MG2 in dissociating gp120 (Bergey et al., 1994 J. Acquired Imm. Defic. Syndr. 7:995–1002).

EXAMPLE 2
Development of an ELISA Method to Assess HIV Inhibitory Glycoproteins The human salivary glycoproteins SAG and MG2 have been reported to play a role in protecting humans against viral infection (Nagashunmugam et al., 1998, J Inf. Dis 178:1635–1641; Bergey et al., 1994, J. Acquired Imm. Defic. Syn. 7:995–1002). SAG and MG2 are both negatively charged glycoproteins containing sialic acid and/or sulfate, and thus may be expected to behave like polyanions such as heparin or dextran sulfate, which are known to inhibit HIV infectivity. SAG was isolated from human submandibular saliva by affinity using the surface sialic acid-specific lectin of *S. gordonii* and the method of Erickson et al. (1983, European J. Biochem. 133:255–261). MG2 was purified from human submandibular saliva using chromatography on Sephadex G 200 (Pharmacia, Piscataway, N.J.) in 6 molar guanidine-HCl, followed by reduction and chromatography on Sephacryl S-300 (Pharmacia, Piscataway, N.J.) in 6 molar urea according to the method of Romausbbu et al. (1991, Biochem. J. 280:341–352).

Figure 4:
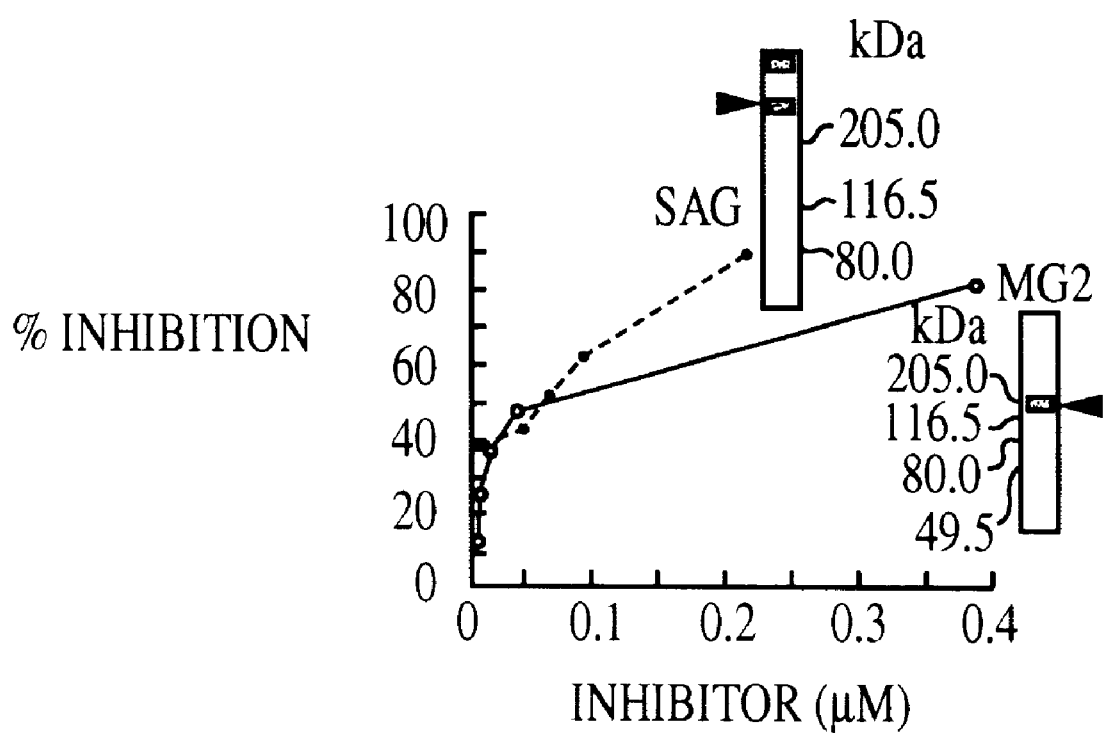
FIG. 4 is a graph depicting the inhibition of HIV-1 infectivity by SAG and MG2. Substantially purified SAG or MG2 was incubated with 50 nanograms of HIV-1$_{IIIB}$ for 3 hours and then added to HeLaCD4 cells. Inhibition of HIV-1 infectivity was assessed as described herein. Blue cells were counted in duplicate wells and % inhibition was calculated relative to wells having virus and cells only. The dashed line represents results of incubation with SAG. The solid line represents results of incubation with MG2.
Figure 5:
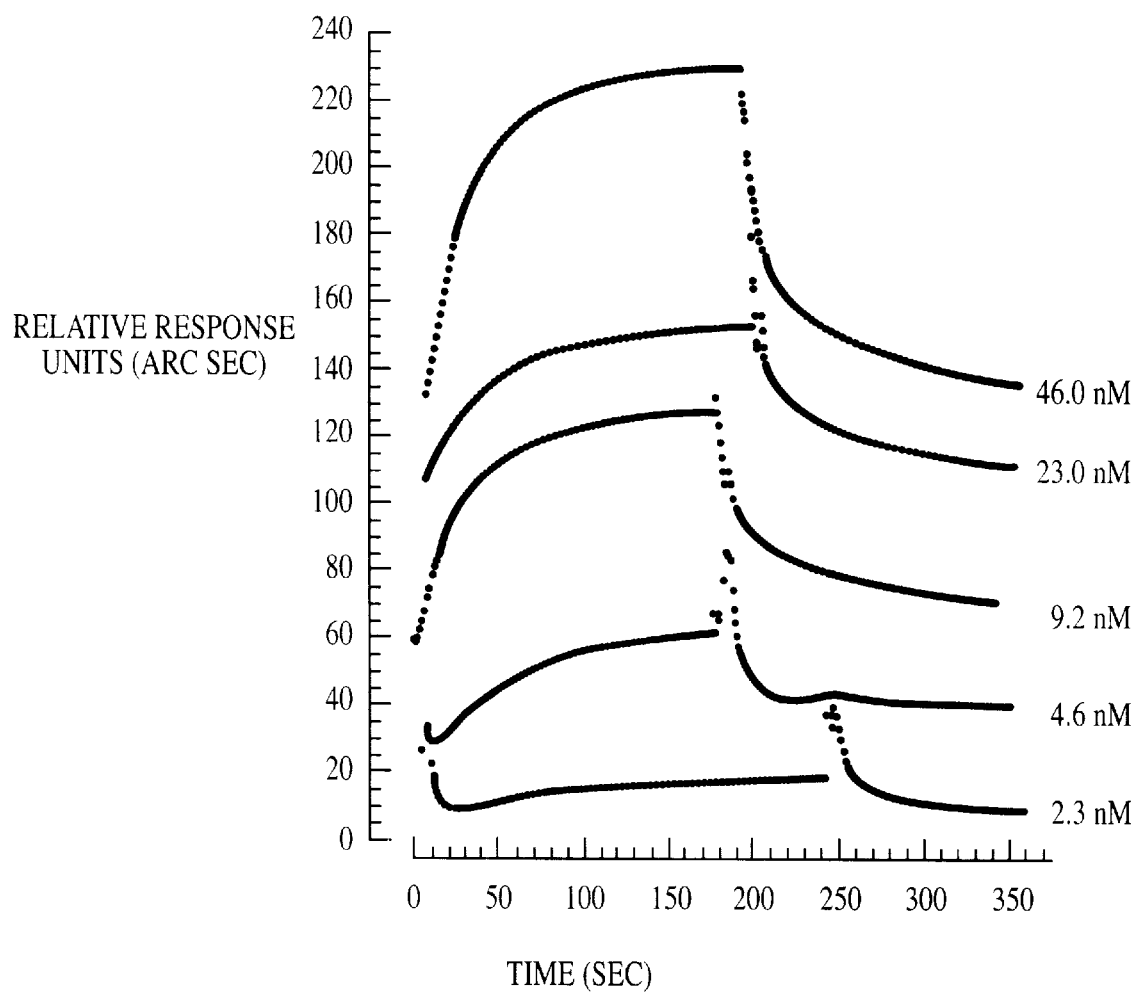
FIG. 5 is a graph depicting the binding response of SAG to gp120 as assessed by the biosensor assay described herein. SAG concentrations tested were 2.3, 4.6, 9.2, 23.0 and 46.0 nanomolar.

To assess the level of purity of the glycoproteins SAG and MG2 after the purification described above, SAG was electrophoresed through a 6% SDS-PAGE gel and MG2 was electrophoresed through a 10% SDS-PAGE gel. Incubation of HIV with both substantially purified SAG and MG2 led to potent dose-dependent inhibition of infection in the HeLaCD4 cell assay as shown in FIG. 4. The substantially purified glycoproteins inhibited HIV infectivity by about 50–90% at levels comparable to their concentration in submandibular saliva. Thus, these two glycoproteins are most likely responsible for the inhibitory activities found in submandibular saliva.

Inhibition of Infection of M-tropic and Orally Transmitted Strains by Salivary Glycoproteins It is believed that the transmission of HIV generally involves M-tropic (macrophage tropic) strains of HIV, and T-tropic (T-cell tropic) strains predominate later in infection. Thus, in order to demonstrate that salivary proteins are effective in preventing the oral transmission of HIV, it is critically important to demonstrate the inhibition of M-tropic primary isolates in vitro since oral transmission of the virus presumably reflects the early stage of infection in a human. The ability of saliva to inhibit infection of PBMCs by a series of M-tropic and T-tropic strains of HIV-1 was therefore assessed. HIV-1 infection of the cells was monitored by p24 production after 5–7 days. In these studies, saliva was effective in inhibiting strains 89.6 (dual tropic), Ada and YU-2 (M-tropic), but not strains Ba-L or SF162 (M-tropic). Thus, saliva "sensitive" and "insensitive" strains of HIV-1 can be isolated. These strains should be very useful for dissecting the binding domains of saliva proteins to gp120, since the insensitive strains may have a gp120 structure lacking the site for SAG or MG2 binding. Four isolates were obtained from individuals considered to have seroconverted after receptive oral-genital contact (Schacker et al., 1996, Ann. Intern. Med. 125:257–264). One of these strains was grown in PBMCs and tested for sensitivity to substantially purified human submandibular saliva. The M-tropic strains YU-2 and Ada were profoundly inhibited by the salivary protein fraction; however, there was no effect of the salivary protein fraction on the level of infection of strain RL1008, obtained from one of the patients in the Schacker study. This finding suggests that there may be subtle differences existing in strains of HIV susceptible to oral transmission. Thus, an alteration in gp120 may render an HIV-1 isolate insensitive to inhibition of infectivity by salivary glycoproteins.

Developing an ELISA Method for the Detection of SAG and MG2 in Saliva Samples

In view of the findings described herein regarding the activity of the salivary glycoproteins SAG and MG2 against HIV-1 infectivity, an ELISA method may be developed which can be used to assess the resistance to HIV-1 infectivity of a patient based on the levels of SAG and MG2 present in the patient's saliva. Patients who are vulnerable to, or who have HIV-1 which exhibit low levels of the salivary glycoproteins SAG and MG2 may be treated for the prevention of HIV-1 infection or the inhibition of HIV-1 infectivity by the administration of a pharmaceutical composition comprising either or both of these glycoproteins to bolster their resistance to HIV-1 infection or infectivity and thereby prevent HIV-1 infection via the oral route.

A sensitive ELISA assay may be developed to quantitate the levels of the salivary glycoproteins SAG and MG2 in a patient's saliva, and to determine if the levels of either or both of these glycoproteins correlates with the amount of inhibition of HIV infectivity in a patient's saliva. In addition, a test may be developed that is simple to administer to a clinical population. A simple method for collection of oral fluids from a representative patient population may also be developed. A direct correlation between inhibition of HIV infectivity in a saliva sample of a patient and the presence of either or both of the glycoproteins SAG and MG2 can then be established as follows.

Whole saliva is collected from, for example, 12 adolescents (6 seronegative, 6 seropositive) and the amount of HIV inhibitory activity in the saliva samples is assessed as described herein. Whole saliva is collected into iced tubes, using parafilm to stimulate salivary flow. The sample is centrifuged at 5,000×g for 10 minutes to pellet particulate material, and the resulting clear supernatant is aliquoted and frozen. To measure the amount of SAG and MG2, the clarified saliva is analyzed by SDS-PAGE followed by Western blotting. Polyclonal antibodies to SAG and MG2 are used in Western blotting. The blots obtained are analyzed by densitometry to quantitate the amounts of the two glycoproteins. The percent inhibition of HIV infectivity is then compared to the levels of SAG and MG2 individually, and SAG and MG2 together, to determine which glycoprotein(s) most closely correlates with the anti-HIV activity.

After correlating the levels of SAG and MG2 with the activity against HIV-1 infectivity in saliva or oral fluid samples as described above, an ELISA method can be developed as follows. Both monoclonal and polyclonal antibodies are available which have demonstrated sensitivity and specificity in Western blotting to both SAG and MG2. Purified SAG and MG2 are used to generate standard curves.

The optimal antigen (glycoprotein) concentration is determined for absorption of antigen onto the plastic of the flat bottom microtiter plates using purified glycoproteins. This establishes the linear range of antigen protein concentration in the ELISA. These experiments are repeated using saliva samples which have been determined by Western blotting to have high or low levels of the glycoproteins SAG and MG2. Saliva samples are also spiked with SAG and MG2 to determine if other proteins in the salivary samples interfere with the ELISA protocol. Assays are optimized for antibody by testing the available monoclonal (approximately 10 antibodies for SAG and 5 for MG2) and polyclonal (4 preparations for SAG, 2 for MG2) antibodies at a range of concentrations. In each case the sensitivity and specificity of the antibody preparation is evaluated. SAG and MG2 are added to standard microtiter plates and an antigen competition enzyme-linked immunoassay is developed using the optimal concentrations of appropriate antibodies as determined herein. Absorbance is read following development of a standard curve. Intrassay and interassay variations are determined. Values obtained by ELISA are compared to those obtained by Western Blotting, and a correlation is established with levels of HIV inhibitory activity being assessed as described herein in samples obtained from 10 individuals. These studies would demonstrate that the ELISA assay is a reliable method for monitoring anti-HIV proteins in human salivary samples and for correlating levels of inhibitory activity against HIV-1 infectivity with the levels of SAG and MG2 glycoproteins in saliva samples obtained from patients.

EXAMPLE 3

Determining the Kinetics of Binding and the Ligands of SAG and MG2 Which Specifically Bind with gp120

In this Example, biosensor assay experiments were conducted to determine the kinetics of binding of the human salivary glycoprotein SAG with the HIV-1 protein gp120 to characterize the nature and strength of the specific binding. Similar experiments may be performed using MG2. The specific ligand or ligands of SAG and MG2 which are capable of specifically binding with gp120 can be determined as described herein. These results will lead to the design of ligands identical or similar to those of SAG and MG2 which are capable of specifically binding with gp120 for use in a pharmaceutical compositions which may be used to inhibit the infectivity of HIV-1 and prevent HIV-1 infection in a patient.

The analysis of protein-protein interactions, such as the binding of salivary proteins to gp120, is ideally studied using biosensor technology. Analyses can be done with small amounts of material, there is no requirement for labeling of the molecules, and kinetic data may be rapidly obtained.

Biosensor technology was thus used to examine the interaction of SAG with immobilized envelope glycoproteins obtained from HIV-2 and SIV and the insensitive M-tropic isolates as controls for non-specific binding. The gp130 of SIVmac239 is available from the AIDS Research and Reference Program and the gp105 from HIV-2 is commercially available (Intracel, Rockville, Md.). These preliminary biosensor experiments have confirmed the specific binding of SAG to gp120 and the fact that the affinity of this interaction is compatible with shedding of gp120 from the virus coat.

Optical biosensor assays were used to assess the binding properties of the substantially purified protein fraction ("Fraction D") prepared from submandibular saliva, and the SAG isolated from this fraction by size exclusion and ion-exchange chromatography as described herein. Biosensors record the binding interaction of macromolecules in real time, allowing for the measurement of the affinity constant ($K_D$) as well as the on and off rate constants. One molecule, the ligand, is immobilized and the binding of the second molecule, the analyte, is monitored over time. Recombinant gp120 was immobilized onto a carboxydextran cuvette through direct amine coupling. This preparation was able to bind soluble CD4 as assessed by the mass (protein) binding upon addition to the cuvette, verifying that the immobilized gp120 was active. Fraction D, obtained from anion exchange chromatography, also demonstrated dose-dependent binding. Since Fraction D contains both SAG and MG2, substantially purified SAG was tested alone to determine whether SAG was able to bind to gp120. Data indicating the binding of SAG to gp120 were obtained and are shown in FIG. 5. The sensogram (graph) depicted in FIG. 5 illustrates the increasing binding response of the biosensor as SAG binds to gp120 as SAG concentration increases. The assay output signal measures the increased mass at the biosensor surface as SAG binds to gp120 immobilized on the surface.

The binding data indicated that both Fraction D and substantially purified SAG bound to immobilized gp120 with affinities similar to that observed for sCD4. The observed kinetics of the binding of SAG versus sCD4 to immobilized gp120 are summarized in Table 1. Substantially purified SAG demonstrated a complex binding pattern having two binding constants, ($K_D$) reflecting high and low affinity sites. The existence of complex binding of SAG as revealed by these data suggests either that there may be multiple binding sites on gp120 for SAG, or that binding of additional SAG molecules to bound SAG can be detected.

Binding Characteristics of Salivary Glycoproteins to HIV Envelope

While the preliminary results of the binding of SAG to immobilized gp120 described in Table 1 suggested that the binding constitutes two $K_D$ values, these initial measurements may be confirmed and extended by the experiments described below using a variety of gp120 proteins obtained from saliva sensitive and insensitive strains and using the BIACORE format. The kinetic binding characteristics of SAG to gp120 is examined by both lAsys (Affinity Sensors, Franklin, Mass.) and BIA 2000 (BIACORE, AB, Piscataway, N.J.) assays to confirm and extend the preliminary measurements. These studies may further establish the kinetics of association of SAG with gp120.

The BIACORE sensor uses global analysis which fits the $K_{on}$ and $K_{off}$ data for all concentrations tested simultaneously, thus providing a better fit of the data. Interaction analysis can also be done in an affinity capture format, for example by covalently immobilizing a non-neutralizing gp120 antibody to the sensor surface, then binding the appropriate target protein non-covalently, and finally adding the bulk phase protein. Unlike direct amine coupling, the advantage of the affinity capture assay is that it allows oriented immobilization of the target protein and hence a more homogeneous surface with which to measure binding.

Binding of salivary proteins to gp120 can be tested for possible competition with the CD4–gp120 interaction. For these experiments, the kinetics of SAG binding to gp120 before and after CD4 addition is assessed. If SAG competes for the same site on gp120 as sCD4, there should be a decrease in the binding response of the second protein.

gp120 is coupled to a sensor cuvette using standard amine coupling. Immobilization levels are kept as low as possible to minimize mass transport effects and steric hindrance. Binding experiments are performed at 25° C. in a buffer at pH 7.4 containing 150 mM NaCl, 10 mM HEPES, 3.4 mM EDTA and 0.005% Tween 20. Association is measured by introducing aliquots of various concentrations of the SAG analyte to the gp120-charged cuvette (IAsys) or flow cell (BIACORE). After the response forms a plateau indicative of a steady state, dissociation of bound protein is monitored upon removing the salivary protein solution and washing the sensor surface with buffer. Remaining SAG is removed and a fully active chip is regenerated with 100 mM phosphoric acid. Data analysis is performed as in Wu et al., 1996, Proc. Natl. Acad. Sci. 93:15030–15035. More complex models than bimolecular are used to fit binding data if necessary (Morton et al., 1995, Anal. Biochem. 227:176). Since the salivary glycoproteins may bind nonspecifically to the chip or to gp120, two types of controls are used: blank chips, shown to bind about 10% SAG as compared to chips with gp120, and immobilized fetuin, an unrelated glycoprotein. Binding of SAG to control chips is subtracted from binding to gp120. Since MG2 has also been shown to inhibit HIV infectivity, the binding of this glycoprotein to immobilized gp120 is assessed and the binding kinetics of this interaction are compared with those obtained using SAG. If specific binding is obtained with MG2, an experiment will be performed to determine if this binding occurs at the same site on gp120 as does binding of SAG to gp120. This experiment constitutes a competition experiment analogous to that described in the case of SAG and CD4.

Identification of gp120 Specific Binding Residues on SAG and MG2

In order to enable the synthetic or enzymatic preparation of the ligand or ligands of SAG or MG2 involved in specific binding with gp120 for use in a pharmaceutical composition for the inhibition of HIV-1 infectivity, the binding residues on SAG or MG2 must be identified. These binding residues can be identified by carrying out the selective removal of carbohydrate residues or amino acid residues from the full glycoprotein of either SAG or MG2 and then assessing the specific binding of the modified glycoprotein to gp120 using a biosensor assay as described herein.

Sialic acid, N-linked or O-linked carbohydrates may be selectively removed from SAG or MG2 and the binding of the modified glycoproteins to gp120 can be assessed using a biosensor assay. Selective carbohydrate residue removal may be carried out using specific enzymes such as neuraminidase, N-glycanase and O-glycosidase to release carbohydrate so that the protein portion of the molecule remains intact. Alterations in the kinetics of association of the modified SAG or MG2 would indicate that the selectively removed residues are involved in specific binding to gp120. For example, if binding is altered by N- but not O-glycanase treatment, the active binding region resides on N-linked carbohydrate structures. Modification of the glycoproteins by limited proteolysis may also be used to identify portions of protein in SAG or MG2 which are key to the specific binding with gp120.

These carbohydrate or protein ligands of SAG or MG2 involved in specific binding with gp120 as identified by a selective removal treatment followed by biosensor experiments as described herein can be assessed for efficacy as part of a pharmaceutical composition for activity against HIV-1 infectivity in assays as described herein. Ligands of SAG or MG2 exhibiting activity against HIV-1 infectivity may be successfully employed as pharmaceutical compositions for the prevention or treatment of HIV-1 infection, to afford a treatment method as described herein which does not require the synthesis of the full glycoprotein or the purification of the glycoprotein from natural or recombinant sources.

TABLE 1

Summary of Kinetic Data

| Analyte/<br>Immobilized Ligand | $k_{on}$<br>$(M^{-1}s^{-1})$ | $k_{off}$<br>$(s^{-1})$ | $K_D$<br>(nM) |
| --- | --- | --- | --- |
| sCD4/gp120 | $7.0 \times 10^5$ | $2.2 \times 10^{-3}$ | 3.1 |
| SAG/gp120 | $30.0 \times 10^5$ | $17.4 \times 10^{-3}$ | 5.8 |
| SAG/gp120 | $8.0 \times 10^5$ | $5.6 \times 10^{-3}$ | 7.0 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting the infectivity of HIV-1, said method comprising
   a) contacting an HIV-1 virion with a composition comprising a substantially purified preparation of a human salivary agglutinin, and
   b) incubating said HIV-1 virion with said human salivary agglutinin for a period of time sufficient to inhibit the infectivity of HIV-1.

2. A composition comprising a carbohydrate ligand of human salivary agglutinin, which is not the entire salivary agglutinin, wherein said ligand is capable of inhibiting infectivity of HIV-1 by specific binding with HIV-1 gp120.

3. The composition of claim 2, wherein said ligand is capable of inhibiting infectivity of HIV-1 by removing gp120 protein from an HIV-1 virion.

4. A method of inhibiting the infectivity of HIV-1, said method comprising
   (a) contacting an HIV-1 virion with a composition comprising a carbohydrate ligand of human salivary agglutinin, which is not the entire salivary agglutinin, wherein said ligand is capable of inhibiting infectivity of HIV-1 by specific binding with HIV-1 gp120, and
   (b) incubating said HIV-1 virion with said composition for a period of time sufficient to inhibit the infectivity of HIV-1.

5. A composition having a surface, having the composition of claim 2 associated with said surface.

6. A kit for detecting a protein which inhibits the infectivity of HIV-1, said kit comprising an antibody which specifically binds with a protein selected from the group consisting of a carbohydrate ligand of human salivary agglutinin which is not the entire salivary agglutinin, and human MG2.

7. The kit of claim 6, wherein said detection reagent is selected from the group consisting of an enzyme and a radionuclide.

8. A method of inhibiting the infectivity of HIV-1, said method comprising
   (a) contacting an HIV-1 virion with a composition having a surface which comprises substantially purified human salivary agglutinin associated with said surface, and
   (b) incubating said HIV-1 virion with said human salivary agglutinin for a period of time sufficient to inhibit the infectivity of HIV-1.

* * * * *